United States Patent
Stump et al.

(10) Patent No.: US 11,430,031 B1
(45) Date of Patent: Aug. 30, 2022

(54) COMPUTING SYSTEM AND METHOD FOR LEVERAGING AGGREGATED INFORMATION TO DETERMINE A UNIFIED PURCHASING SOLUTION

(71) Applicant: MCKESSON CORPORATION, Irving, TX (US)

(72) Inventors: John Stump, Carrollton, TX (US); Christopher Shain, Fenton, MO (US); Andrew Wilson, Richmond, VA (US); Kevin Scheckelhoff, Richmond, VA (US); Gregg Niemiec, San Antonio, TX (US); Matthew Bates, Alpharetta, GA (US); Jennifer Luker, Justin, TX (US)

(73) Assignee: MCKESSON CORPORATION, Irving, TX (US)

( * ) Notice: Subject to any disclaimer, the term of this patent is extended or adjusted under 35 U.S.C. 154(b) by 323 days.

(21) Appl. No.: 16/836,484

(22) Filed: Mar. 31, 2020

(51) Int. Cl.
G06Q 30/06 (2012.01)
G06F 16/2457 (2019.01)
(Continued)

(52) U.S. Cl.
CPC ... *G06Q 30/0605* (2013.01); *G06F 16/24578* (2019.01); *G06Q 20/085* (2013.01);
(Continued)

(58) Field of Classification Search
None
See application file for complete search history.

(56) References Cited

U.S. PATENT DOCUMENTS 8,050,941 B2 * 11/2011 Hardaway ............ G06Q 10/087
705/28
8,370,173 B2 * 2/2013 Hardaway .............. G16H 70/40
705/2
(Continued)

OTHER PUBLICATIONS

Anon., "Prime Vendor Program, SUNRx Partner to Provide 340B Technology to Health Centers, Hospitals Nationwide," Business Wire [New York] Jul. 7, 2010. (Year: 2010).*
(Continued)

*Primary Examiner* — Nicholas D Rosen
(74) *Attorney, Agent, or Firm* — Alston & Bird LLP

(57) ABSTRACT

A computing system and method leverage aggregated information regarding historical medication usage and medication availability to efficiently determine a unified purchasing solution. In a method, an order is received for a quantity of a medication. For a covered entity, a portion of the quantity of the medication that is able to be satisfied pursuant to a 340B program is determined based upon information regarding historical usage of the medication for outpatients and prior purchases under the 340B program. The method also includes determining the portions that are separately able to be satisfied pursuant to a group purchasing organization (GPO) program and a wholesaler/prime vendor program. The method further includes determining a proposed purchasing solution and to cause information regarding the proposed purchasing solution to be provided including information regarding savings based upon the prices of the medication for a respective period of time that was provided by the supplier.

19 Claims, 5 Drawing Sheets

(51) Int. Cl.
*G16H 50/70* (2018.01)
*G16H 70/40* (2018.01)
*G06Q 20/08* (2012.01)
*G06Q 50/26* (2012.01)
*G06Q 30/02* (2012.01)

(52) U.S. Cl.
CPC ..... *G06Q 30/0206* (2013.01); *G06Q 30/0607* (2013.01); *G06Q 30/0635* (2013.01); *G06Q 50/265* (2013.01); *G16H 50/70* (2018.01); *G16H 70/40* (2018.01)

(56) References Cited

U.S. PATENT DOCUMENTS

| | | | |
|---|---|---|---|
| 10,566,087 B1 | 2/2020 | Puckett | |
| 10,685,390 B1 | 6/2020 | Puckett | |
| 10,720,234 B1* | 7/2020 | Leonardi | G06Q 30/0207 |
| 11,361,862 B2 | 6/2022 | Puckett | |
| 2006/0080274 A1* | 4/2006 | Mourad | G06Q 30/02 |
| 2008/0306796 A1* | 12/2008 | Zimmerman | G06Q 10/063 |
| | | | 705/7.11 |
| 2009/0094051 A1* | 4/2009 | Ard | G16H 70/40 |
| | | | 705/2 |
| 2009/0281823 A1* | 11/2009 | Hardaway | G06Q 10/087 |
| | | | 705/2 |
| 2009/0281824 A1* | 11/2009 | Hardaway | G16H 20/13 |
| | | | 705/2 |
| 2009/0326975 A1* | 12/2009 | Hardaway | G06Q 10/10 |
| | | | 705/2 |
| 2012/0239463 A1* | 9/2012 | Wertz | G06Q 10/06375 |
| | | | 705/7.39 |
| 2014/0358578 A1* | 12/2014 | Ptachcinski | G06Q 10/10 |
| | | | 705/2 |
| 2015/0278924 A1* | 10/2015 | Maurer | G06Q 30/0635 |
| | | | 705/26.81 |
| 2016/0042147 A1 | 2/2016 | Maurer et al. | |
| 2020/0105392 A1* | 4/2020 | Karkazis | G16H 50/30 |
| 2021/0056496 A1* | 2/2021 | Gajeski | G06Q 10/0833 |

OTHER PUBLICATIONS

Quintaro, P., "Allergan Expands Access to IUDs for Millions of Underserved Women in the US by Announcing Agreement with Apexus for Nationwide Distribution of LILETTA(R) (levonorgestrel-releasing intrauterine system) 52 mg," Benzinga.com Sep. 10, 2015. (Year: 2015).*

Anon., "Opportunities and Strategies for Improving Pharmacy Financial Performance," Healthcare Financial Management 73.6; SS1 (4). Healthcare Financial Management Association, Jun. 2019. (Year: 2019).*

Stein, M.M., "CMS Details Hospital 340B Acquisition Cost Data Survey," Inside Washington Publishers' Inside CMS, 23.7 Inside Washington Publishers. Feb. 13, 200. (Year: 2020).*

Stein, M.M., "340B Hospitals Ask CMS to Suspend Cuts, Drug Cost Survey," InsideHealthPolicy.com's Daily Brief, Inside Washington Publishers. Mar. 26, 2020. (Year: 2020).*

System Data Systems, Inc., "Sentry Data Systems ignites innovation engine: Announces groundbreaking patent for care improvement and cost reduction technology", Cision PR Newswire, Apr. 23, 2019, 3 pages, retrieved from https://www.prnewswire.com/news-releases/sentry-data-systems-ignites-innovation-engine-announces-groundbreaking-patent-for-care-improvement-and-cost-reduction-technology-300835956.html on Apr. 24, 2020.

* cited by examiner

Total Quantity: X

| <u>340B</u> | <u>GPO</u> | <u>Wholesaler Pricing</u> |
|---|---|---|
| Quantity: X1 | Quantity: X2 | Quantity: X3 |
| Per Unit Price: Y1 | Price Per Unit: Y2 | Price Per Unit: Y3 |

Total Price: Y

Figure 5

COMPUTING SYSTEM AND METHOD FOR LEVERAGING AGGREGATED INFORMATION TO DETERMINE A UNIFIED PURCHASING SOLUTION

TECHNOLOGIAL FIELD

An example embodiment relates generally to a computing system, method and computer program product for efficiently determining a unified purchasing solution and, more particularly, to a computing system, method and computer program product for leveraging aggregated information regarding historical usage and availability of a medication in order to efficiently determine the unified purchasing solution.

BACKGROUND

Health care providers, such as hospitals, health care facilities, health care practices, health care organizations or the like, regularly order a wide variety of medications from one or more suppliers, such as one or more wholesalers or other sources of the medication. The medication may be ordered pursuant to a variety of different pricing programs, each of which may offer a different pricing structure. One such program is the 340B drug pricing program. The 340B drug pricing program was created by the United States government and requires drug manufacturers to provide outpatient drugs to eligible health care organizations and covered entities at reduced prices. The 340B drug pricing program may therefore offer pricing advantages for a medication, but only for certain medications, such as medications prescribed to outpatients by a covered entity, and, even then, only a predefined quantity of the medication during a predefined period of time in at least some situations.

Although a 340B drug pricing program oftentimes offers pricing advantages for a medication to a covered entity, the same medication may sometimes be purchased by a health care provider pursuant to other pricing programs at even more favorable pricing. However, the ordering process for medication by a health care provider is oftentimes not optimized in terms of the pricing to paid for the medication such that the healthcare provider sometimes pays more for the medication and, as a result, loses that savings opportunity.

Additionally, since a health care provider may order medication from a plurality of different sources, no single source of the medication generally has complete information as to the order history of the health care provider. Thus, any one source of the medication for the health care provider may have only a limited amount of information regarding the total medication purchases by the health care provider and, as a result, is unable to facilitate optimization of the order by the health care provider.

BRIEF SUMMARY

A computing system, method and computer program product are provided in accordance with an example embodiment in order to leverage aggregated information regarding historical usage of a medication by a health care provider and information regarding availability of the medication from a supplier to efficiently determine a unified purchasing solution. The unified purchasing solution may permit the health care provider to purchase the medication that has been ordered in the least expensive manner so as to increase the resulting savings enjoyed by the health care provider. The computing system, method and computer program product of an example embodiment are configured to determine the unified purchasing solution in an efficient manner that conserves both computing resources and network resources by utilizing the aggregated information from both the health care providers that are placing orders and suppliers of the medication to determine a unified purchasing solution without requiring messages from repeatedly being constructed and transmitted between the health care provider placing the order and the one or more suppliers from which the health care provider orders medication in an effort to determine, among other things, pricing and availability of the medication from the supplier(s) pursuant to the various pricing programs.

In an example embodiment, a computer-implemented method is provided for leveraging aggregated information regarding historical usage of a medication and information regarding availability of the medication to determine a unified purchasing solution. The computer-implemented method includes accessing data of a supplier of a medication to determine a purchase price and one or more reference prices of the medication and receiving an order from a health care provider for a quantity of a medication. For a health care provider that is a covered entity, the method includes determining a portion of the quantity of the medication that is able to be satisfied pursuant to a 340B program based upon information regarding historical usage of the medication for outpatients and prior purchases of the medication pursuant to the 340B program. The method also includes determining a portion of the quantity of the medication that is able to be satisfied pursuant to a group purchasing organization (GPO) program based upon prior purchases of the medication pursuant to the GPO program and determining a portion of the quantity of the medication that is able to be satisfied pursuant to a wholesaler/340B prime vendor pricing program (WAC). The method further includes determining the proposed purchasing solution based upon the respective portions of the quantity of the medication that are able to be satisfied pursuant to the 340B, GPO and wholesaler/prime vendor programs and prices of the medication pursuant to the 340B, GPO and wholesaler/prime vendor programs. The method additionally includes causing information regarding the unified purchasing solution to be provided including information regarding savings provided by the proposed purchasing solution based upon the purchase price and the one or more reference prices of the medication for a respective period of time that were provided by the supplier.

The method of an example embodiment also includes determining that the medication is an orphan drug that is to be purchased pursuant to a manufacturer's voluntary orphan drug pricing program and determining the information regarding the savings based upon a comparison of a price of the orphan drug that is purchased pursuant to the manufacturer's voluntary orphan drug pricing program to a price of the orphan drug that is purchased pursuant to the GPO program. In another example embodiment, the method receives an order for a quantity of medication by receiving an order for a first generic medication and determining if there is a second generic medication that is equivalent to the first generic medication. In this example embodiment, the method also includes determining the information regarding savings opportunities based upon a comparison of a weighted price of the second generic medication purchased from the 340B, GPO and wholesaler/prime vendor programs based upon historical purchases by pricing program pursuant to the proposed purchasing solution to the a weighted price and quantities of the first generic medication purchased from each of the 340B, GPO and wholesaler/prime vendor program accounts pursuant to the same proposed purchasing solution.

The method of an example embodiment determines the portion of the quantity of the medication that is able to be satisfied pursuant to a 340B program by determining whether the medication is a covered outpatient drug and, in an instance in which the medication is a covered outpatient drug, an anticipated quantity of the medication to be dispensed to outpatients based upon the historical usage of the medication for outpatients. In this example embodiment, the determination of the portion of the quantity of the medication that is able to be satisfied pursuant to a 340B program also includes limiting, based upon the prior purchases of the medication pursuant to the 340B program, the medication available to the health care provider pursuant to the 340B program so as not to a exceed a predefined maximum in the aggregate during a predefined period of time. Also, in this example embodiment, the method may determine the anticipated quantity of the medication to be dispensed to outpatients by accessing data of the covered entity regarding the historical usage of the medication for outpatients.

The method of an example embodiment may determine the portion of the quantity of the medication that is able to be satisfied pursuant to a GPO program by limiting the medication available pursuant to the GPO program based upon the prior purchases of the medication pursuant to the GPO program so as not to a exceed a predefined maximum in the aggregate. The method of an example embodiment also includes accessing data of a supplier of the medication to determine an inventory of the medication. In this example embodiment, the method determines the respective portions of the quantity of the medication that is able to be satisfied pursuant to the 340B, GPO and wholesaler/prime vendor programs based at least partially on the inventory of the medication. The method of an example embodiment determines the proposed purchasing solution by determining a combination of the medication to be provided pursuant to one or more of the 340B, GPO and wholesaler/prime vendor programs that satisfies the quantity specified by the order and that also satisfies a predefined pricing objective. The information regarding the unified purchasing solution may be caused to be provided in real time or near real time relative to receipt of the order.

In another embodiment, a computing system is provided that is configured to leverage aggregated information regarding historical usage of a medication and information regarding availability of the medication to determine a unified purchasing solution. The computing system includes processing circuitry and at least one memory including computer program code with the at least one memory and the computer program code configured to, with the processing circuitry, cause the computing system to access data of a supplier of a medication to determine a purchase price and one or more reference prices of the medication and receive an order from a health care provider for a quantity of the medication and, for a health care provider that is a covered entity, determine a portion of the quantity of the medication that is able to be satisfied pursuant to a 340B program based upon information regarding historical usage of the medication for outpatients and prior purchases of the medication pursuant to the 340B program. The computing system is also caused to determine a portion of the quantity of the medication that is able to be satisfied pursuant to a group purchasing organization (GPO) program based upon prior purchases of the medication pursuant to the GPO program and to determine a portion of the quantity of the medication that is able to be satisfied pursuant to a wholesaler/prime vendor program. The computing system is further configured to determine the proposed purchasing solution based upon the respective portions of the quantity of the medication that are able to be satisfied pursuant to the 340B, GPO and wholesaler/prime vendor programs and prices of the medication pursuant to the 340B, GPO and wholesaler/prime vendor programs and to cause information regarding the unified purchasing solution to be provided including information regarding savings provided by the proposed purchasing solution based upon the purchase price and the one or more reference prices of the medication for a respective period of time that were provided by the supplier.

The computing system of an example embodiment is caused to determine that the medication is an orphan drug that is to be purchased pursuant to manufacturer voluntary orphan drug pricing program and to determine the information regarding the savings based upon a comparison of a price of the orphan drug that is purchased pursuant to the manufacturer voluntary orphan drug pricing program to a price of the orphan drug that is purchased pursuant to the GPO program. In another example embodiment, the computing system is configured to receive an order for a quantity of medication by receiving an order for a first generic medication and determining if there is a second generic medication that is equivalent to the first generic medication. In this example embodiment, the computing system is caused to determine the information regarding savings opportunities based upon a comparison of a weighted price of the second generic medication purchased from the 340B, GPO and wholesaler/prime vendor programs based upon historical purchases by pricing program pursuant to the proposed purchasing solution to the a price of the first generic medication purchased from each of the 340B, GPO and wholesaler/prime vendor program account pursuant to the same proposed purchasing solution.

The at least one memory and the computer program code are configured to, with the processing circuitry, cause the computing system of an example embodiment to determine the portion of the quantity of the medication that is able to be satisfied pursuant to a 340B program by determining whether the medication is a covered outpatient drug and, in an instance in which the medication is a covered outpatient drug, an anticipated quantity of the medication to be dispensed to outpatients based upon the historical usage of the medication for outpatients. Based upon the prior purchases of the medication pursuant to the 340B program, the computing system of this example embodiment is also configured to limit the medication available to the covered entity pursuant to the 340B program so as not to a exceed a predefined maximum in the aggregate during a predefined period of time. In this example embodiment, the at least one memory and the computer program code are also configured to, with the processing circuitry, cause the computing system to determine the anticipated quantity of the medication to be dispensed to outpatients by accessing data of the covered entity regarding the historical usage of the medication for outpatients.

The at least one memory and the computer program code are configured to, with the processing circuitry, cause the computing system of an example embodiment to determine the portion of the quantity of the medication that is able to be satisfied pursuant to a GPO program by limiting the medication available pursuant to the GPO program based upon the prior purchases of the medication pursuant to the GPO program so as not to a exceed a predefined maximum in the aggregate during a predefined period of time. The at least one memory and the computer program code are further configured to, with the processing circuitry, cause the computing system of an example embodiment to access data of a supplier of the medication to determine an inventory of the medication. In this example embodiment, the at least one memory and the computer program code are configured to, with the processing circuitry, cause the computing system to determine the portions of the quantity of the medication that are able to be satisfied pursuant to the 340B, GPO and wholesaler/prime vendor programs at least partially based on the inventory of the medication.

The at least one memory and the computer program code are configured to, with the processing circuitry, cause the computing system of an example embodiment to determine the proposed purchasing solution by determining a combination of the medication to be provided pursuant to one or more of the 340B, GPO and wholesaler/prime vendor programs that satisfies the quantity specified by the order and that also satisfies a predefined pricing objective. The information regarding the unified purchasing solution may be caused to be provided in real time or near real time relative to receipt of the order.

In a further example embodiment, a computer program product is provided that is configured to leverage aggregated information regarding historical usage of a medication and information regarding availability of the medication to determine a unified purchasing solution. The computer program product includes at least one non-transitory computer-readable storage medium having computer-executable program code instructions stored therein with the computer-executable program code instructions including program code instructions configured to access data of a supplier of a medication to determine a purchase price and one or more reference prices of the medication and receive an order from a health care provider for a quantity of the medication and, for a health care provider that is a covered entity, program code instructions configured to determine a portion of the quantity of the medication that is able to be satisfied pursuant to a 340B program based upon information regarding historical usage of the medication for outpatients and prior purchases of the medication pursuant to the 340B program. The computer-executable program code instructions also include program code instructions configured to determine a portion of the quantity of the medication that is able to be satisfied pursuant to a group purchasing organization (GPO) program based upon prior purchases of the medication pursuant to the GPO program and program code instructions configured to determine a portion of the quantity of the medication that is able to be satisfied pursuant to a wholesaler/prime vendor program. The computer-executable program code instructions further include program code instructions configured to determine the proposed purchasing solution based upon the respective portions of the quantity of the medication that are able to be satisfied pursuant to the 340B, GPO and wholesaler/prime vendor programs and prices of the medication pursuant to the 340B, GPO and wholesaler/prime vendor programs and program code instructions configured to cause information regarding the unified purchasing solution to be provided including information regarding savings provided by the proposed purchasing solution based upon the purchase price and one or more reference prices of the medication for a respective period of time that were provided by the supplier.

The program code instructions of an example embodiment are further configured to determine that the medication is an orphan drug that is to be purchased pursuant to manufacturer voluntary orphan drug pricing program and to determine the information regarding the savings based upon a comparison of a price of the orphan drug that is purchased pursuant to the manufacturer's voluntary orphan drug pricing program to a price of the orphan drug that is purchased pursuant to the GPO program. In another example embodiment, the program code instructions configured to receive an order for a quantity of medication include program code instructions configured to receive an order for a first generic medication and to determine if there is a second generic medication that is equivalent to the first generic medication. In this example embodiment, the program code instructions may also be configured to determine the information regarding savings opportunities based upon a comparison of a weighted price of the second generic medication purchased from the 340B, GPO and wholesaler/prime vendor programs based upon historical prices and quantities of the first generic medication purchased from the 340B, GPO and wholesaler/prime vendor programs pursuant to the same proposed purchasing solution.

The program code instructions configured to determine the portion of the quantity of the medication that is able to be satisfied pursuant to a 340B program may include program code instructions configured to determine whether the medication is a covered outpatient drug and, in an instance in which the medication is a covered outpatient drug, an anticipated quantity of the medication to be dispensed to outpatients based upon the historical usage of the medication for outpatients. In this example embodiment, the program code instructions configured to determine the portion of the quantity of the medication that is able to be satisfied pursuant to a 340B program may also include program code instructions configured to limit, based upon the prior purchases of the medication pursuant to the 340B program, the medication available to the covered entity pursuant to the 340B program so as not to a exceed a predefined maximum in the aggregate during a predefined period of time. Additionally, in this example embodiment, the program code instructions configured to determine the anticipated quantity of the medication to be dispensed to outpatients include program code instructions configured to access data of the covered entity regarding the historical usage of the medication for outpatients. The information regarding the unified purchasing solution may be caused to be provided in real time or near real time relative to receipt of the order.

In an example embodiment, a computing system is provided that is configured to address any premium paid pursuant to a wholesaler/prime vendor program versus the GPO purchasing program. The computing system includes processing circuitry and at least on memory including computer program code with the at least one memory and the computer program code configured to, with the processing circuitry, cause the computing system to access data of a supplier of one or more medications to determine a price of the one or more medications pursuant to a plurality of pricing programs. The computing system is also caused to determine a price of one or more medications that are purchased pursuant to the wholesaler/prime vendor program and to determine a price of the one or more medications in the event that the one or more medications had alternatively been purchased pursuant to a group purchasing organization (GPO) program. The computing system is further configured to determine the premium for a respective one of the one or more medications that is paid pursuant to the wholesaler/prime vendor program relative to the GPO program and to cause a presentation to be provided upon a user interface including information regarding one or more causes for the premium and information regarding one or more potential solutions to reduce the premium. The one or more causes are at least partially based upon the respective medication and a type of health care provider that is purchasing the respective medication. A corresponding method and computer program product are also provided.

The at least one memory and the computer program code are configured to, with the processing circuitry, cause the computing system of an example embodiment to cause the presentation to the provided by causing information to be presented regarding the one or more medications and the premiums determined for the respective medications. In an example embodiment, the at least one memory and the computer program code are configured to, with the processing circuitry, cause the computing system to cause information to be presented by causing the information regarding the one or more medications to be presented in a ranked order based upon the premiums determined for the respective medications. In an example embodiment, the information regarding one or more causes for the premium comprise information regarding why the respective medication was purchased pursuant to the wholesaler/prime vendor program instead of the GPO program.

BRIEF DESCRIPTION OF THE DRAWINGS

Figure 1:
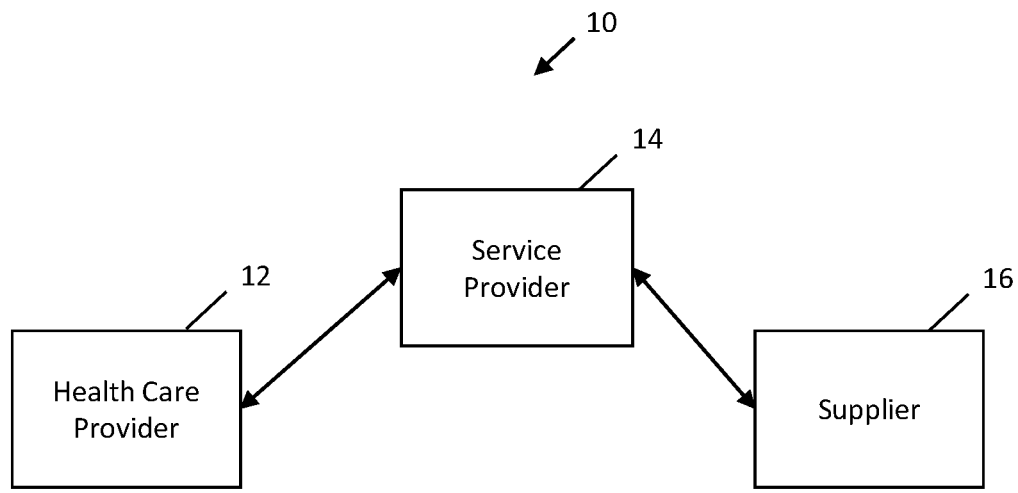
Figure 2:
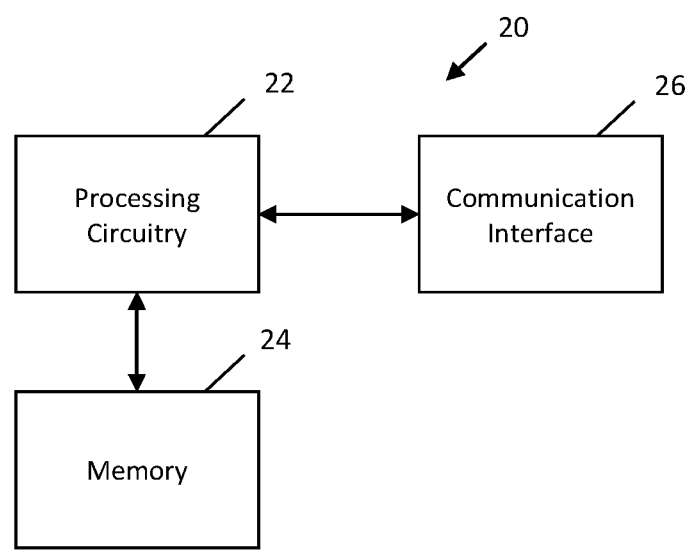
Figure 3:
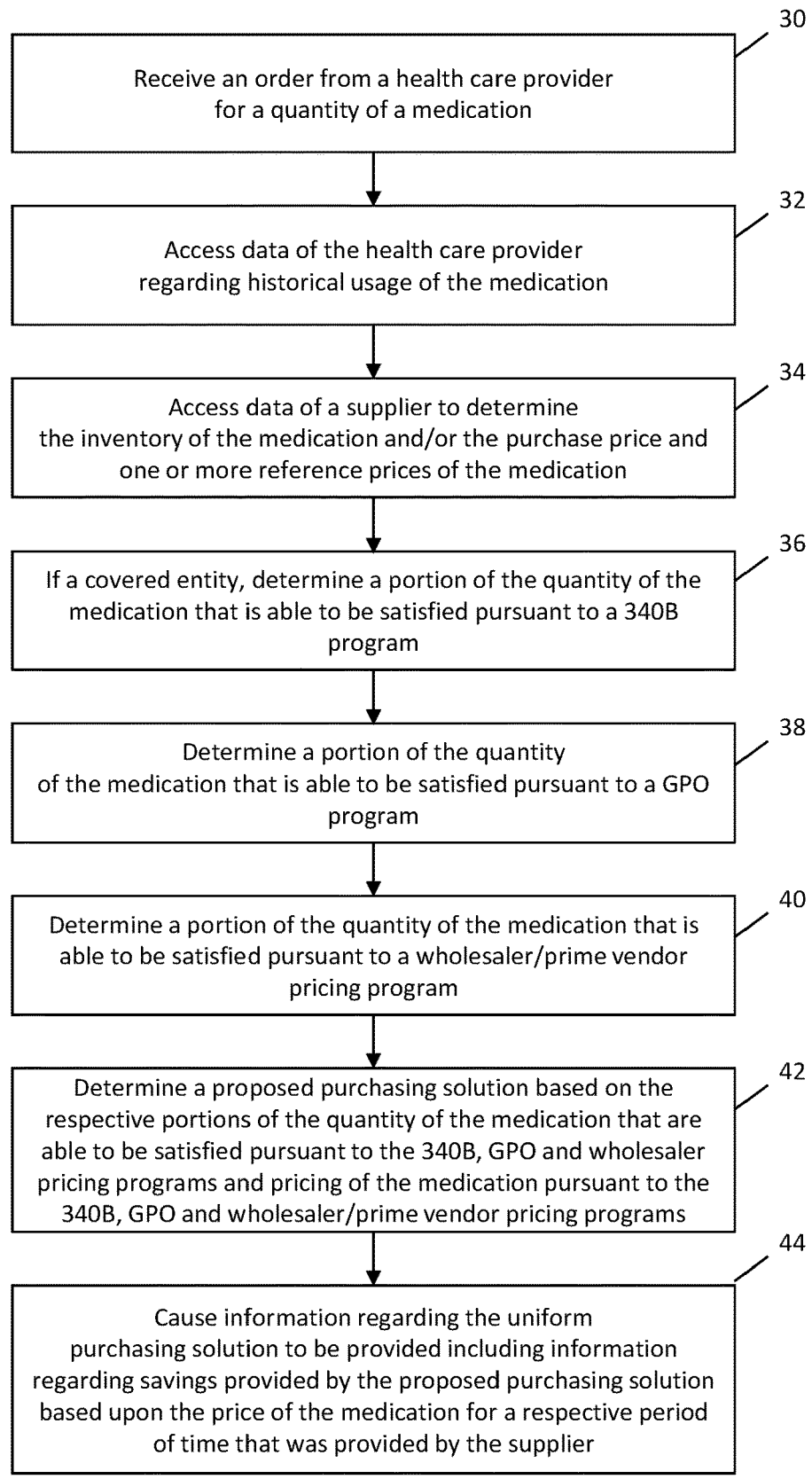
Figure 4:
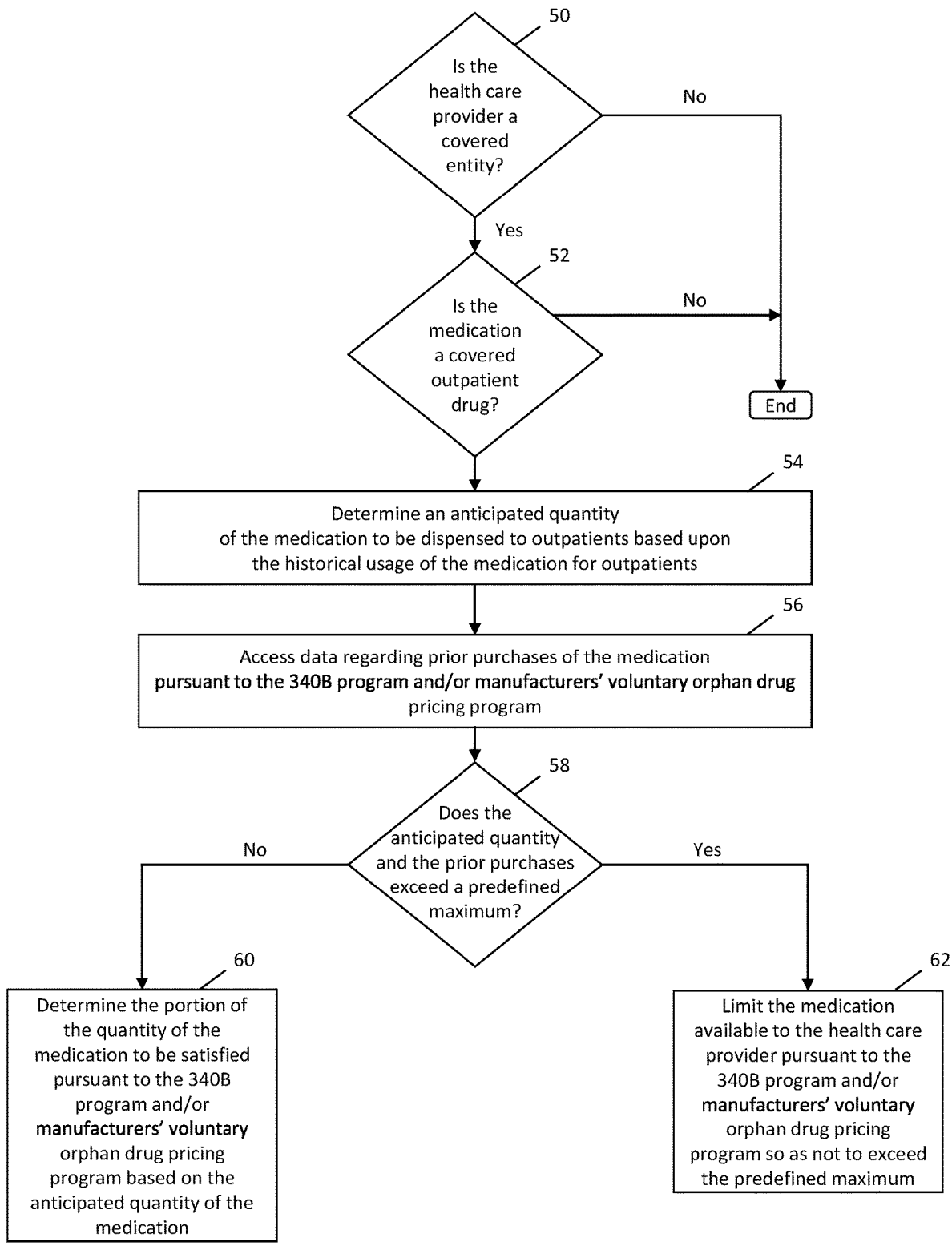
Figure 6:
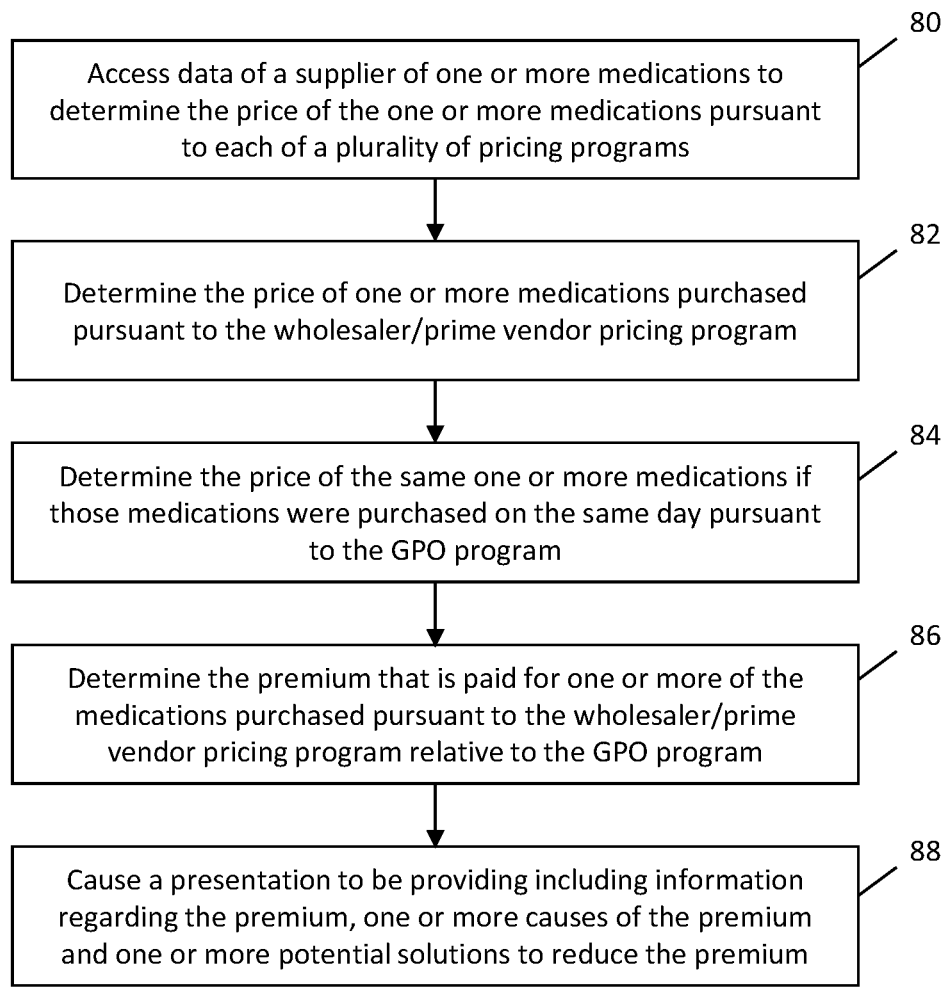

Having thus described certain embodiments of the present disclosure in general terms, reference will now be made to the accompanying drawings, which are not necessarily drawn to scale, and wherein:

FIG. 1 is a diagram of system illustrating the relationship of a 340B service provider in accordance with an example embodiment relative to a supplier of a medication and a health care provider that places an order for the medication;

FIG. 2 is a block diagram of a computing system of a 340B service provider in accordance with an example embodiment;

FIG. 3 is a flow chart illustrating the operations performed, such as by the computing system of the 340B service provider, to determine a unified purchasing solution in accordance with an example embodiment;

FIG. 4 is a flow chart illustrating the operations performed, such as by the computing system of the 340B service provider, to determine a portion of the quantity of the medication that was ordered that may be satisfied by a 340B pricing program in accordance with an example embodiment;

FIG. 5 illustrates a user interface that depicts a unified purchasing solution that has been determined in accordance with an example embodiment; and FIG. 6 is a flow chart illustrating the operations performed, such as by the computing system, to determine a premium paid pursuant to a wholesaler/prime vendor program in accordance with an example embodiment.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described herein to receive a message or data from another computing device or entity, it will be appreciated that the message or data may be received directly from the other computing device and/or may be received indirectly via one or more intermediary computing devices, such as, for example, one or more servers, relays, routers, network access points, and/or the like. Similarly, where a computing device is described herein to transmit a message or data to another computing device or entity, it will be appreciated that the message or data may be sent directly to the other computing device or entity or may be sent to the other computing device or entity via one or more interlinking computing devices, such as, for example, one or more servers, relays, routers, network access points, and/or the like.

A computing system, method and computer program product are provided in accordance with an example embodiment in order to leverage aggregated information regarding historical usage of a medication and information regarding availability of the medication to determine a unified purchasing solution for the medication. By way of example, but not of limitation, a system 10 in which a computing system, method and computer program product of an example embodiment may be deployed is depicted in FIG. 1. As shown, the system includes a health care provider 12, a service provider 14 and one or more suppliers 16. In this regard, although a single supplier is depicted in FIG. 1, the system may include a plurality of suppliers.

The health care provider 12 of an example embodiment may be a hospital, a health care facility, a health care organization or other type of health care provider that prescribes medications to patients, at least some of which are outpatients. As discussed below, the health care provider may be a covered entity as defined by the 340B program. The suppliers 16 are configured to provide medication to the health care provider in response to an order, that is, a purchase order, issued by the health care provider. The supplier may be a wholesaler of the medication or any of a variety of other sources of the medication that is the subject of the order.

The service provider 14 is configured to process orders issued by the health care provider 12 and is embodied by a computing system 20, an example of which is depicted in FIG. 2. As shown in FIG. 2, the computing system includes, is associated with or is in communication with processing circuitry 22, memory 24 and communication interface 26.

In some example embodiments, the memory 24 may include one or more non-transitory memory devices such as, for example, volatile and/or non-volatile memory that may be either fixed or removable. In this regard, the memory may comprise a non-transitory computer-readable storage medium. It will be appreciated that while the memory is illustrated as a single memory, the memory may comprise a plurality of memories. The plurality of memories may be embodied on a single computing device or may be distributed across a plurality of computing devices. The memory may be configured to store information, data, applications, computer program code, instructions and/or the like for enabling the computing system 20 to carry out various functions in accordance with one or more example embodiments. For example, the memory may be configured to store computer program code for performing corresponding functions of the service provider 14, as described herein according to example embodiments.

The memory 24 may be further configured to buffer input data for processing by the processing circuitry 22. Additionally, or alternatively, the memory may be configured to store instructions for execution by the processing circuitry. In some embodiments, the memory may include one or more databases that may store a variety of files, contents, or data sets, such as but not limited to historical data of the health care provider 12 and/or inventory data of the supplier(s) 16. Among the contents of the memory, applications may be stored for execution by the processing circuitry to carry out the functionality associated with each respective application. In some cases, the memory may be in communication with one or more of the processing circuitry and/or communication interface 26 for passing information among components of computing system 20.

The processing circuitry 22 may be embodied in a number of different ways. For example, the processing circuitry may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processing circuitry may be configured to execute instructions stored in the memory 24 or otherwise accessible to the processing circuitry. As such, whether configured by hardware or by a combination of hardware and software, the processing circuitry may represent an entity (e.g., physically embodied in circuitry) specifically configured to perform operations according to embodiments of the present invention while configured accordingly. Thus, for example, when the processing circuitry is embodied as an ASIC, FPGA or the like, the processing circuitry may be specifically configured hardware for conducting the operations described herein. Alternatively, as another example, when the processing circuitry is embodied as an executor of software instructions, the instructions may specifically configure the processing circuitry to perform the operations described herein.

The communication interface 26 may include one or more interface mechanisms for enabling communication with other devices and/or networks. In some cases, the communication interface may be any means such as a device or circuitry embodied in either hardware, or a combination of hardware and software that is configured to receive and/or transmit data from/to a network and/or any other device or module in communication with the processing circuitry 22. By way of example, the communication interface may be configured to enable communication amongst the health care provider 12, the service provider 14 and the supplier(s) 16 over a network. Accordingly, the communication interface may, for example, include supporting hardware and/or software for enabling wireless and/or wireline communications via cable, digital subscriber line (DSL), universal serial bus (USB), Ethernet, or other methods.

The network, such as the network in which the system of FIG. 1 or components thereof or components described herein may operate, (e.g., health care provider 12, service provider 14, supplier 16, and/or the like) may include a local area network, the Internet, any other form of a network, or in any combination thereof, including proprietary private and semi-private networks and public networks. The network may comprise a wired network and/or a wireless network (e.g., a cellular network, wireless local area network, wireless wide area network, some combination thereof, and/or the like).

Referring now to FIG. 3, the operations performed, such as by the computing system 20 of the service provider 14, are illustrated. As shown in block 30, the computing system, such as the processing circuitry 22, the communication interface 16 or the like, is configured to receive an order, such as purchase order, from a health care provider 12 for a quantity of a medication. The medication may be any of a variety of prescribed medications, such as prescription drugs or other pharmaceutical products. The order that is received generally identifies one or more medications and a quantity of each medication that is requested by the health care provider.

As shown in block 32, the computing system 20, such as the processing circuitry 22, the memory 24, the communication interface 26 or the like, may also be configured to access data of the health care provider 12 regarding historical usage of the medication that is identified by the order. This historical data may have been previously provided by the health care provider and stored by the memory. In this instance, the processing circuitry is configured to access the data regarding historical usage the medication by retrieving the data from memory. Alternatively, the data may be maintained by the health care provider and/or may be stored by an external database. In this instance, the processing circuitry is configured to access the data via the communication interface in order to retrieve the data regarding historical usage of the medication. Regardless of the location of the data, the data regarding the historical usage of the medication can include various types of information. For example, the data regarding the historical usage of the medication may identify the portion of the medication that has historically been prescribed by the health care provider for use by outpatients and the portion of the medication that has been historically been prescribed by the health care provider for use by inpatients. Historical utilization will also include other data elements such as pricing source (340B, GPO and WAC), reference pricing for 340B and WAC purchases, hospital charge data, National Drug Code (NDC) and wholesaler item number detail. As used herein, reference pricing refers to the price for the same medication that is purchased pursuant to a 340B or wholesaler/prime vendor pricing program under the GPO pricing program on the same day as the purchase and/or to the price for the same medication that is purchased pursuant to a wholesaler/prime vendor pricing program under the 340B pricing program on the same day as the purchase.

As shown in block 34, the computing system 20, such as the processing circuitry 22, the memory 24, the communication interface 26 or the like, is also configured to access data of a supplier 16 to determine the inventory and/or stock status maintained by the supplier of the medication and the price charged by the supplier for the medication during respective periods of time, such as on different days. In one embodiment, this inventory data may have been previously provided by the supplier and stored by the memory. In this instance, the processing circuitry is configured to access the data regarding inventory of the supplier of the medication by retrieving the data from memory. Alternatively, the data may be maintained by the supplier and/or may be stored by an external database. In this instance, the processing circuitry is configured to access the data via the communication interface in order to retrieve the data regarding inventory of the supplier of the medication.

The computing system 20, such as the processing circuitry 22, is configured in accordance with an example embodiment to determine the uniform purchasing solution by considering a plurality of different purchasing options offered by a plurality of pricing programs. The plurality of pricing programs that are evaluated in accordance with an example embodiment include the 340B drug pricing program, a group purchasing organization (GPO) program and a wholesaler/prime vendor program. Prior to determining the availability of the medication pursuant to a 340B pricing program, however, the computing system 20, such as the processing circuitry 22, is configured to determine whether the health care provider 12 that submitted the order is a covered entity pursuant to the 340B pricing program. A covered entity is a facility or program eligible to purchase discounted medication through the 340B pricing program and includes a plurality of categories of hospitals and non-hospitals. In order to identify the health care provider that submitted the order as a covered entity, the computing system, such as the memory 24, may maintain a listing of the covered entities such that the processing circuitry may compare the identity of the health care provider that submitted the order to the listing of covered entities in order to determine whether the health care provider is a covered entity. Alternatively, the health care provider may provide, either concurrent with the order or separate therefrom, information from which the computing system, such as the processing circuitry, can confirm that the health care provider is a covered entity.

In an instance in which the health care provider 12 is a covered entity, the computing system 20, such as the processing circuitry 22, is configured to determine the portion of the quantity of the medication that is able to be satisfied pursuant to the 340B program. See block 36 of FIG. 3. Although the portion of the quantity of the medication that is able to be satisfied pursuant to the 340B program may be determined in various manners, FIG. 4 depicts the operations performed, such as by the computing system and, more particularly, the processing circuitry, of an example embodiment, in order to determine the portion of the quantity of the medication that is able to be satisfied pursuant to the 340B program and the processing of orphan drugs. As described above and as illustrated in block 50 of FIG. 4, the computing system, such as the processing circuitry, is configured to determine whether the health care provider is a covered entity. In an instance in which the health care provider is not a covered entity, the process concludes and the computing system, such as the processing circuitry, is configured to determine that no portion of the quantity of the medication is able to be satisfied pursuant to the 340B program since the health care provider does not quality to participate in the 340B program.

If the health care provider 12 that submitted the order is a covered entity, however, the computing system 20, such as the processing circuitry 22, is configured to determine whether the medication is a covered outpatient drug so as to be eligible pursuant to the 340B program. See block 52 of FIG. 4. The covered outpatient drugs are statutorily defined and the computing system, such as the processing circuitry, may be configured to determine whether the medication is a covered outpatient drug in various manners including by comparing the medication to a listing of covered outpatient drugs stored by the memory 24 and/or stored by an external database accessible via the communications interface 26. In an instance in which the medication is not a covered outpatient drug, the computing system and processing circuitry determine if the medication is an orphan drug. If the medication is not an orphan drug this process concludes and the computing system, such as the processing circuitry, is configured to determine that no portion of the quantity of the medication is able to be satisfied pursuant to the 340B program or voluntary manufacturer orphan drug pricing program since the medication does not quality to be provided pursuant to the 340B program and the Food and Drug Administration (FDA) orphan drug definition.

However, if the health care provider 12 is a covered entity and the medication is a covered outpatient drug, the computing system 20, such as the processing circuitry 22, is configured to determine the anticipated quantity of the medication to be dispensed to outpatients based upon the historical usage and/or billing of the medication by the health care provider for outpatients. If the health provider is a covered entity and the medication is an orphan drug the computing system, such as the processing circuitry, will determine outpatient utilization similar to that for covered outpatient drugs. See block 54 of FIG. 4. In this regard, the computing system, such as the processing circuitry, is configured to review the data of the health care provider regarding the historical usage of the medication that is the subject of the order and to identify the percentage of the medication prescribed historically by the health care provider that has been utilized by outpatients, as opposed to inpatients. This determination may be made based upon all historical data that has been collected by the health care provider or that portion of the historical data for certain period of time, such as a most recent predefined period of time, e.g., the past year, the past six months or the like. For example, based upon the historical usage data of the health care provider for the medication, the computing system, such as the processing circuitry, may determine that X % of the medication was prescribed for use by outpatients and (100−X) % of the medication was prescribed for use by inpatients. As such, the computing system, such as the processing circuitry, of this example embodiment is configured to determine the anticipated quantity of the medication that is to be dispensed to outpatients to be the same percentage of the quantity of the medication that was the subject of the order, such as by determining the product of X % and the quantity of the medication included in the order. For example, if the order requested 100 units of the medication, the computing system, such as the processing circuitry, is configured to determine that X % of the 100 units is anticipated to be dispensed to outpatients based upon the historical usage of the same medication by the health care provider.

As shown in block 56 of FIG. 4, the computing system 20, such as the processing circuitry 22, the memory 24 or the like, is also configured to access data regarding prior purchases of the covered outpatient medication pursuant to the 340B program and orphan drugs pursuant to the manufacturer's voluntary orphan drug pricing program. In this example embodiment, a health care provider that is a covered entity may only purchase a predefined maximum amount of a medication pursuant to the 340B program. In an example embodiment, the predefined maximum amount of the medication that may be purchased by a covered entity is defined for a predefined period of time. Thus, the computing system, such as the processing circuitry, is configured to determine the quantity of the medication that has previously been purchased by the health care provider pursuant to the 340B program, such as the quantity the medication that has previously been purchased by the health care provider pursuant to the 340B program during the predefined period of time. The data regarding the prior purchases may have been provided by the health care provider and stored by memory 24 such that the processing circuitry may access the data stored by memory to determine the quantity of the medication that was previously purchased pursuant to a 340B program. Alternatively, data regarding the prior purchases may be stored by the health care provider or provided to an external database such that the processing circuitry may access the data stored by the health care provider or by an external database via the communication interface 26 to determine the quantity of the medication that was previously purchased pursuant to a 340B program. In the case of orphan drugs, the computing system, such as the processing circuitry, is configured to determine the quantity of the medication that has previously been purchased by the health care provider pursuant to the manufacturer's voluntary orphan drug pricing program, such as the quantity the medication that has previously been purchased by the health care provider pursuant to the manufacturer's voluntary orphan drug pricing program during the predefined period of time.

As shown in decision block 58, the computing system 20, such as the processing circuitry 22, is configured to determine whether the sum of the anticipated quantity of the medication that has been ordered that is to be dispensed to outpatients and the quantity of prior purchases of the same medications exceed the predefined maximum quantity of the medication that may be purchased by the health care provider 12 pursuant to the 340B program for covered outpatient drugs. In other words, the computing system, such as the processing circuitry, is configured to determine whether the additional purchase of the medication that has been ordered pursuant to the 340B program will cause the health care provider to have purchased more units of the medication pursuant to the 340B program, if the order were filled, than is allowed by the 340B program. In an instance in which the sum does not exceed, the predefined maximum quantity of the medication that may be purchased by a covered entity pursuant to the 340B program, the computing system, such as the processing circuitry, is configured to define the portion of the quantity of the medication that is the subject of the order that may be purchased pursuant to the 340B program based upon the anticipated quantity of the medication, such as by being equal to the anticipated quantity of the medication. See block 60. The computing system, such as the processing circuitry, is also configured to similarly process orphan drugs pursuant to the manufacturer's voluntary orphan drug pricing program.

However, if the sum exceeds the predefined maximum quantity of the covered medication that may be purchased by the health care provider 12 pursuant to the 340B program, the computing system 20, such as the processing circuitry 22, is configured to limit the medication available to the health care provider so as not to exceed the predefined maximum quantity. See block 62. In this regard, the computing system, such as the processing circuitry, is configured to define the portion of the quantity of the medication that is provided pursuant to the 340B program to be less than the anticipated quantity of the medication that is to be dispensed to outpatients and, in an example embodiment, to be no more than an amount that is equal to the quantity of the medication that in combination with the quantity of the same medication that was previously purchased by the health care provider pursuant to the 340B program equals the predefined maximum quantity. For example, in an instance in which the predefined maximum quantity is defined as $Q_{max}$, the anticipated quantity of medication to be dispensed to outpatients is defined as $Q_{history}$ and the quantity of the prior purchases of the same medication pursuant to the 340B program is defined as $Q_{prior}$, the portion of the quantity of the medication that is able to be satisfied pursuant to the 340B program is equal to $Q_{history}$ in an instance in which $(Q_{history}+Q_{prior}) \leq Q_{max}$. However, in an instance in which $(Q_{history}+Q_{prior}) > Q_{max}$, the portion of quantity of the medication that is to be satisfied pursuant to 340B program is defined to be no greater than and, in some embodiments, equal to $(Q_{max}-Q_{prior})$. The computing system, such as the processing circuitry, is also configured to similarly process orphan drugs pursuant to the manufacturer's voluntary orphan drug pricing program.

The computing system 20, such as the processing circuitry 22, is also configured to determine the portion of the quantity of the medication that is able to be satisfied pursuant to a GPO program. See block 38 of FIG. 3. In some instances, the availability of medications pursuant to GPO program is also limited to a predefined maximum quantity of the medication that may be provided pursuant to the GPO program, at least within a predefined period of time. As such, the computing system, such as the processing circuitry is configured to access data regarding prior purchases by the health care provider 12 pursuant to the GPO program, such as based upon data provided by or accessible from the health care provider. Based upon this data regarding prior purchases of the medication pursuant to the GPO program, the computing system, such as the processing circuitry, is configured to determine whether the quantity of the medication that has been ordered in combination with the total quantity of the same medication that has previously been purchased by the health care provider pursuant to the GPO program, such as the total amount of the medication that has previously purchased by the health care provider pursuant to the GPO program within a predefined time period, exceeds the predefined maximum quantity of the medication that may be purchased pursuant to the GPO program.

In an instance in which the predefined maximum quantity of medication that may be purchased pursuant to the GPO program is exceeded, the computing system 20, such as the processing circuitry 22, defines the portion of the medication that may be purchased pursuant to the GPO program to be equal to the difference between the predefined maximum quantity of the medication that may be purchased pursuant to the GPO program and the quantity of the same medication that has been previously purchased pursuant to the GPO program, such as within the predefined time period. Alternatively, in an instance in which the predefined maximum quantity of medication that may be purchased pursuant to the GPO program is not exceeded, the computing system, such as the processing circuitry, is configured to determine the portion of the medication that may be purchased pursuant to the GPO program to be equal to the quantity of the medication requested by the order.

The computing system 20, such as the processing circuitry 22, is also configured to determine the portion of the quantity of the medication that may be satisfied by a wholesaler/prime vendor program, such as programs that sell medication at the wholesaler acquisition cost (WAC), the average wholesaler price (AWC), 340B prime vendor price or the like. See block 40. The wholesaler/prime vendor program has no minimum or maximum quantities and is used as the default in the event no 340B pricing program and/or GPO pricing program quantities are available at the time of order.

In conjunction with determining the availability of the medication pursuant to any of the pricing programs, the inventory of the medication that is maintained by the supplier 16 may also be taken into account, such as based upon data provided by the supplier or otherwise accessible by the processing circuitry 22 as described above. In this regard, the computing system 20, such as the processing circuitry, is configured to limit the portion of the quantity of the medication pursuant to each of the pricing programs, both individually and in combination, to be no more than the quantity of the medication maintained in inventory by the supplier at the current moment in time. In this regard, the computing system, such as the processing circuitry, is configured to compare the quantity of the medication that has been ordered to the quantity of the medication that is maintained in inventory by the supplier. In an instance in which the quantity of medication that has been ordered is less than the quantity of the medication that is maintained in inventory, the portion of the quantity of the medication that has been ordered that may be satisfied by the plurality of pricing programs may be determined as described above and is not limited based upon the inventory of the supplier. However, in an instance in which the quantity of medication that has been ordered is greater than the quantity of the medication that is maintained in inventory, the computing system, such as the processing circuitry, is configured to limit the total quantity that may be provided pursuant to the plurality of pricing programs in combination to be no more than the quantity of the medication that is maintained in inventory of the supplier.

As shown in block 42, the computing system 20, such as the processing circuitry 22, is configured to determine a proposed purchasing solution based on the respective portions of the quantity of the medication that are able to be satisfied pursuant to the 340B, GPO and wholesaler/prime vendor programs and prices of the medication pursuant to the 340B, GPO and wholesaler/prime vendor programs. In this regard, the computing system, such as the processing circuitry, is configured to determine the quantity of medication to be purchased pursuant to each of the pricing programs such that: (i) the total quantity of the medications equals the quantity of medication requested by the order (unless the quantity of medication that may be purchased is limited by the inventory of the supplier 16 in which case, the total quantity of the medications is no greater than and may equal the quantity of the medication maintained by the supplier), (ii) the quantity of medication provided pursuant to each pricing program does not exceed the portion of the medication that was determined to be able to be satisfied pursuant to the respective pricing programs and (iii) any other requirements of the respective pricing programs, such as a predefined minimum quantity of the medication that may be applicable with respect to the wholesaler/prime vendor program, are satisfied, while also satisfying a predefined pricing objective. For example, the predefined pricing objective may be that the medication is purchased in various quantities from one or more of the pricing programs such that the medication can be purchased at the lowest cost by the health care provider 12.

While the 340B program is designed to provide medication at reduced prices in certain circumstances, the pricing negotiated pursuant to a GPO program or that is available pursuant to a wholesaler/prime vendor pricing program may, in some instances be less expensive for certain medications. Thus, the purchase of additional quantities of medication pursuant to the GPO and/or wholesaler/prime vendor pricing program may be advisable in some circumstances as opposed to always ordering the maximum quantity of medication that is permissible pursuant to the 340B program.

The computing system 20, such as the processing circuitry 22, the communication interface 26 or the like, is also configured to cause information regarding the uniform purchasing solution to be provided. See block 44. The information that is provided includes information regarding the savings provided by the proposed purchasing solution based upon the price of the medication for a respective period of time, such as the date of purchase, that was provided by the supplier. In this regard, the computing system, such as the processing circuitry, is configured in accordance with an example embodiment to compare the price for the medication pursuant to the proposed purchasing solution utilizing the different pricing programs to the price for the medication if the medication were purchased from the supplier pursuant to the wholesaler/prime vendor pricing program on the same day as the actual purchase (i.e., WAC price versus GPO price). Thus, utilizing the daily wholesaler prices for medication purchased pursuant to the 340B and wholesaler/prime vendor pricing programs relative to the reference prices for the same medication on the same day, that is, the price for the same medication on the same day pursuant to the GPO pricing program, the savings or premium provided by the proposed purchasing solution may be presented.

As shown, by way of example, in FIG. 5, the information may be provided via a user interface 70, such as a web page provided by the 340B service provider 14, such as the computing system 20, and accessible by the health care provider 12. As shown, the uniform pricing solution may identify the quantity and the unit price of medication that is suggested to be provided pursuant to each of the different pricing programs in order to supply the total quantity (or at least the maximum quantity permitted by the inventory of the supplier 16) that was requested by the order. The information provided in conjunction with the uniform purchasing solution may also identify the total price if the medication was purchased pursuant to the uniform purchasing solution and, in some embodiments, may also identify the savings to the health care provider that are occasioned by adopting the uniform purchasing solution as opposed to rigidly following the purchasing program(s) identified for purchase of the medication by the order. Consequently, the unified purchasing solution may permit the health care provider to purchase the medication that has been ordered in the least expensive manner so as to increase the resulting profit enjoyed by the health care provider following payment or other reimbursement for the sale of the medication.

The computing system 20 and method of an example embodiment may offer particular advantages in relation to the analysis of pricing and savings relative to orphan drugs and generic drugs and the development of proposed purchasing solutions therefore. In relation to orphan drugs, a list of orphan drugs may be maintained that includes the names of the orphan drugs as provided by the Food and Drug Administration (FDA) and the corresponding National Drug Codes (NDCs). The list of orphan drugs may also be supplemented based upon information provided by drug manufacturers regarding medications that are equivalent to those identified by the FDA. Although orphan drugs are not included within the definition of covered drugs as provided by the 340B program, the manufacturers of the orphan drugs may have manufacturers' voluntary orphan drug pricing programs that treat the pricing of the orphan drugs consistent with, e.g., similar or identical to, the pricing provided by the 340B program. As such, the list of orphan drugs may also be supplemented by 340B pricing information provided by the manufacturers and the wholesalers for the respective orphan drugs. This list of orphan drugs may be periodically updated.

In this example embodiment, following the receipt of the order, the computing system 20, such as the processing circuitry 22, is configured to determine that the medication is an orphan drug that is eligible to be purchased pursuant to the manufacturer voluntary orphan drug pricing program. In this regard, the medication may be determined to be an orphan drug by comparison to the list of orphan drugs. As described above, a purchasing solution for the orphan drug is then determined based upon the consideration of the plurality of pricing programs including the manufacturer voluntary orphan drug pricing program and historical data provided by the health care provider 12 regarding the historical usage of the orphan drug for inpatient and outpatient scenarios and also based upon the prior purchases pursuant to the different pricing programs. In an example embodiment, the computing system, such as the processing circuitry, is then configured to determine the information regarding the savings offered by the proposed purchasing solution based upon a comparison of a price of the orphan drug that is purchased pursuant to the manufacturer voluntary orphan drug pricing program to a price of the orphan drug that is purchased pursuant to a different pricing program, such as the GPO program.

In another example embodiment relating to generic medications, the computing system 20 and method are configured to determine the savings that may be realized by ordering a different, but equivalent, generic medication. In this regard, a list may be created based upon information provided by database vendors and/or pharmaceutical manufacturers of the generic medications with an indication as to which generic medications are equivalent to one another as well as the associated NDCs. The list of generic medications may also be supplemented with pricing information provided by the wholesaler/prime vendor, GPO and 340B pricing programs for the respective generic medications pursuant to each of the plurality of different pricing programs. This list of generic medications may be periodically updated.

In response to receipt an order for a quantity of medication, the computing system 20, such as the processing circuitry 22, is configured to determine that the medication is a first generic medication, such as based upon a comparison to the list of generic medications, and to also determine one or more second generic medications that are equivalent to the first generic medication, such as also based upon a review of the list of generic medications. As described above, a purchasing solution for the first generic medication is then determined based upon the consideration of the plurality of pricing programs and historical data provided by the health care provider 12 regarding the historical usage of the orphan drug for inpatient and outpatient scenarios and also based upon the prior purchases pursuant to the different pricing programs. In this regard, the computing system, such as the processing circuitry, is then configured to determine a weighted price for the first generic medication. The weighted price is the average price for the first generic medication after having taken into account the different quantities of the first generic medication that were purchased through each of the plurality of pricing programs and the prices at which the first generic medication was purchased pursuant to the plurality of pricing programs. A weighted price for the other generic medications, such as the second generic medication, that are equivalent to the first generic medication is also determined utilizing the same ratio of purchases from the different pricing programs that was established for the first generic medication and the prices for the other generic medications pursuant to the various pricing programs.

In an example embodiment, the computing system 20, such as the processing circuitry 22, is then configured to determine information regarding the savings based upon a comparison of a weighted price of the second generic medication purchased from the 340B, GPO and wholesaler/prime vendor programs pursuant to the proposed purchasing solution to the price of the first generic medication purchased from the 340B, GPO and wholesaler/prime vendor programs pursuant to the same proposed purchasing solution. Thus, utilizing the same weighting or ratio between the 340B, GPO and wholesaler/prime vendor program, the savings offered by ordering the second generic medication, instead of the first generic medication may be illustrated. In embodiments in which this comparison is performed in real time or near real time in conjunction with an order by a health care provider 12, the health care provider may be provided an opportunity to alter the order so as to order the second generic medication instead of the first generic medication and to enjoy the savings.

In another example embodiment depicted in FIG. 6, a computing system 20 and method are provided that are configured to identify a premium paid pursuant to a wholesaler/prime vendor program. The computing system, such as the processing circuitry 22, is configured to access data of a supplier of one or more medications to determine a price of the one or more medications pursuant to each of a plurality of pricing programs. See block 80. This pricing information may be provided for a respective period of time, such as on a daily basis. From this data, the computing system, such as the processing circuitry, is caused to determine a price of one or more medications that are purchased pursuant to the wholesaler/prime vendor program and to determine a price of the same one or more medications if those same medication(s) had been alternatively been purchased on the same day pursuant to a GPO program. See blocks 82 and 84. The computing system, such as the processing circuitry, is further configured to determine the premium for a respective one of the one or more medications that is paid pursuant to the wholesaler/prime vendor program relative to the GPO program, that is, to determine the amount in excess of the price for a medication provided pursuant to the GPO program that is paid for the same medication on the same day pursuant to the wholesaler/prime vendor program. See block 86. Finally, the computing system, such as the processing circuitry, of this example embodiment is configured to cause a presentation to be provided upon a user interface including information regarding the premium, one or more causes for the premium and one or more potential solutions to reduce the premium. See block 88.

There may be many different causes for the premiums and many different solutions for reducing the premiums. However, the one or more causes are at least partially based upon the respective medication and a type of health care provider that is purchasing the respective medication. By way of example, insulin may typically be purchased by certain types of health care providers in a relatively large vial and pursuant to a wholesaler/prime vendor program. In a hospital setting, insulin may be prescribed for a patient and the vial may be sent to the inpatient care area. However, the patient may only be administered a small amount of insulin from the vial. In this situation, the health care provider may only bill for the amount of insulin that was administered with the remainder of the vial ultimately being wasted without going through the billing process. Thus, the cause associated with the WAC premium may be related to unbilled/uncompensated waste, while a proposed solution may be to consider utilizing insulin pens for appropriate patients and billing the entire pen at the time of dispense thereby resulting in reduced waste.

The presentation may also include information regarding the one or more medications and the premiums determined for the respective medications in addition to the causes and potential solutions for the premiums. In an example embodiment, the information regarding the one or more medications may be presented in a ranked order based upon the premiums determined for the respective medications, such as in descending order with the medication having the largest associated premium listed first.

In an example embodiment, the information regarding one or more causes for the premium comprises information regarding why the respective medication was purchased pursuant to the wholesaler/prime vendor program instead of the GPO program. There are instances where an incorrectly entered billing code in the hospital billing system could result in an item going unbilled because of the discrepancy and subsequently resulting in a WAC purchase associated with a premium.

As described above, a computing system 20, method and computer program product are provided in order to leverage aggregated information regarding historical usage of a medication by a health care provider 12 and information regarding availability of the medication from a supplier 16 to efficiently determine a unified purchasing solution. The computing system, method and computer program product of an example embodiment are configured to determine the unified purchasing solution in an efficient manner that conserves both computing resources and network resources by utilizing the aggregated information from both the health care providers that are placing orders and suppliers of the medication to determine a unified purchasing solution without requiring messages from repeatedly being constructed and transmitted between the health care provider placing the order and the one or more suppliers from which the health care provider orders medication in an effort to determine, among other things, pricing and availability of the medication from the supplier(s) pursuant to the various pricing programs.

As noted above, FIGS. 3, 4 and 6 are flowcharts illustrating the operations performed by a method, computing system 20 and computer program product in accordance with one embodiment of the present invention. It will be understood that each block of the flowcharts, and combinations of blocks in the flowcharts, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory 24 of a computing system 20 employing an embodiment of the present invention and executed by a processing circuitry 22 of the computing system. As will be appreciated, any such computer program instructions may be loaded onto a computer or other programmable apparatus (e.g., hardware) to produce a machine, such that the resulting computer or other programmable apparatus provides for implementation of the functions specified in the flowchart blocks. These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks. As such, the operations of FIGS. 3, 4 and 6, when executed, convert a computer or processing circuitry into a particular machine configured to perform an example embodiment of the present invention. Accordingly, the operations of FIGS. 3, 4 and 6 define an algorithm for configuring a computer or processing circuitry, e.g., processor, to perform an example embodiment. In some cases, a general purpose computer may be provided with an instance of the processor which performs the algorithm of FIGS. 3, 4 and 6 to transform the general purpose computer into a particular machine configured to perform an example embodiment.

Accordingly, blocks of the flowcharts support combinations of means for performing the specified functions and combinations of operations for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions. In some embodiments, certain ones of the operations above may be modified or further amplified and additional optional operations may be included. It should be appreciated that each of the modifications, optional additions or amplifications below may be included with the operations above either alone or in combination with any others among the features described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method for leveraging aggregated information regarding historical usage of a medication and information regarding availability of the medication to determine a unified purchasing solution, the computer-implemented method comprising:

accessing data of a supplier of a medication to determine a purchase price and one or more reference prices of the medication;

receiving an order from a health care provider for a quantity of the medication;

for a health care provider that is a covered entity, determining a portion of the quantity of the medication that is able to be satisfied pursuant to a 340B program based upon information regarding historical usage of the medication for outpatients and prior purchases of the medication pursuant to the 340B program;

determining a portion of the quantity of the medication that is able to be satisfied pursuant to a group purchasing organization (GPO) program based upon prior purchases of the medication pursuant to the GPO program;

determining a portion of the quantity of the medication that is able to be satisfied pursuant to a wholesaler/prime vendor program;

determining a proposed purchasing solution based upon the respective portions of the quantity of the medication that are able to be satisfied pursuant to the 340B, GPO and wholesaler/prime vendor programs and prices of the medication pursuant to the 340B, GPO and wholesaler/prime vendor programs; and causing information regarding the unified purchasing solution to be provided including information regarding savings provided by the proposed purchasing solution based upon the purchase price and the one or more reference prices of the medication for a respective period of time that were provided by the supplier.

2. A computer-implemented method according to claim 1 further comprising:

determining that the medication is an orphan drug that is to be purchased pursuant to a manufacturer's voluntary orphan drug pricing program; and determining the information regarding the savings based upon a comparison of a price of the orphan drug that is purchased pursuant to the manufacturer's voluntary orphan drug pricing program to a price of the orphan drug that is purchased pursuant to the GPO program.

3. A computer-implemented method according to claim 1 wherein receiving an order for a quantity of medication comprises receiving an order for a first generic medication and determining if there is a second generic medication that is equivalent to the first generic medication, and wherein the method further comprises determining the information regarding the savings based upon a comparison of a weighted price of the second generic medication purchased from the 340B, GPO and wholesaler/prime vendor programs pursuant to the proposed purchasing solution to a weighted price of the first generic medication purchased from the 340B, GPO and wholesaler/prime vendor programs pursuant to the same proposed purchasing solution.

4. A computer-implemented method according to claim 1 wherein determining the portion of the quantity of the medication that is able to be satisfied pursuant to a 340B program comprises:

determining whether the medication is a covered outpatient drug and, in an instance in which the medication is a covered outpatient drug, an anticipated quantity of the medication to be dispensed to outpatients based upon the historical usage of the medication for outpatients; and based upon the prior purchases of the medication pursuant to the 340B program, limiting the medication available to the health care provider pursuant to the 340B program so as not to a exceed a predefined maximum in the aggregate during a predefined period of time.

5. A computer-implemented method according to claim 4 wherein determining the anticipated quantity of the medication to be dispensed to outpatients comprises accessing data of the covered entity regarding the historical usage of the medication for outpatients.

6. A computer-implemented method according to claim 1 wherein determining the portion of the quantity of the medication that is able to be satisfied pursuant to a GPO program comprises limiting the medication available pursuant to the GPO program based upon the prior purchases of the medication pursuant to the GPO program so as not to a exceed a predefined maximum in the aggregate.

7. A computer-implemented method according to claim 1 wherein the information regarding the unified purchasing solution is caused to be provided in real time or near real time relative to receipt of the order.

8. A computing system configured to leverage aggregated information regarding historical usage of a medication and information regarding availability of the medication to determine a unified purchasing solution, the computing system comprising processing circuitry and at least one memory including computer program code, the at least one memory and the computer program code configured to, with the processing circuitry, cause the computing system to at least:

access data of a supplier of a medication to determine a purchase price and one or more reference prices of the medication;

receive an order from a health care provider for a quantity of the medication;

for a health care provider that is a covered entity, determine a portion of the quantity of the medication that is able to be satisfied pursuant to a 340B program based upon information regarding historical usage of the medication for outpatients and prior purchases of the medication pursuant to the 340B program;

determine a portion of the quantity of the medication that is able to be satisfied pursuant to a group purchasing organization (GPO) program based upon prior purchases of the medication pursuant to the GPO program;

determine a portion of the quantity of the medication that is able to be satisfied pursuant to a wholesaler/prime vendor program;

determine a proposed purchasing solution based upon the respective portions of the quantity of the medication that are able to be satisfied pursuant to the 340B, GPO and wholesaler/prime vendor programs and prices of the medication pursuant to the 340B, GPO and wholesaler/prime vendor programs; and cause information regarding the unified purchasing solution to be provided including information regarding savings provided by the proposed purchasing solution based upon the purchase price and one or more reference prices of the medication for a respective period of time that were provided by the supplier.

9. A computing system according to claim 8 wherein the at least one memory and the computer program code are further configured to, with the processing circuitry, cause the computing system to:

determine that the medication is an orphan drug that is to be purchased pursuant to a manufacturer's voluntary orphan drug pricing program; and determine the information regarding the savings based upon a comparison of a price of the orphan drug that is purchased pursuant to the manufacturer's voluntary orphan drug pricing program to a price of the orphan drug that is purchased pursuant to the GPO program.

10. A computing system according to claim 8 wherein the at least one memory and the computer program code are configured to, with the processing circuitry, cause the computing system to receive an order for a quantity of medication by receiving an order for a first generic medication and to determine if there is a second generic medication that is equivalent to the first generic medication, and wherein the at least one memory and the computer program code are further configured to, with the processing circuitry, cause the computing system to determine the information regarding the savings based upon a comparison of a weighted price of the second generic medication purchased from the 340B, GPO and wholesaler/prime vendor programs pursuant to the proposed purchasing solution to a weighted price of the first generic medication purchased from the 340B, GPO and wholesaler/prime vendor programs pursuant to the same proposed purchasing solution.

11. A computing system according to claim 8 wherein the at least one memory and the computer program code are configured to, with the processing circuitry, cause the computing system to determine the portion of the quantity of the medication that is able to be satisfied pursuant to a 340B program by:
    determining whether the medication is a covered outpatient drug and, in an instance in which the medication is a covered outpatient drug, an anticipated quantity of the medication to be dispensed to outpatients based upon the historical usage of the medication for outpatients; and
    based upon the prior purchases of the medication pursuant to the 340B program, limiting the medication available to the covered entity pursuant to the 340B program so as not to a exceed a predefined maximum in the aggregate during a predefined period of time.

12. A computing system according to claim 11 wherein the at least one memory and the computer program code are configured to, with the processing circuitry, cause the computing system to determine the anticipated quantity of the medication to be dispensed to outpatients by accessing data of the covered entity regarding the historical usage of the medication for outpatients.

13. A computing system according to claim 8 wherein the at least one memory and the computer program code are configured to, with the processing circuitry, cause the computing system to determine the portion of the quantity of the medication that is able to be satisfied pursuant to a GPO program by limiting the medication available pursuant to the GPO program based upon the prior purchases of the medication pursuant to the GPO program so as not to a exceed a predefined maximum in the aggregate during a predefined period of time.

14. A computing system according to claim 8 wherein the at least one memory and the computer program code are configured to, with the processing circuitry, cause the computing system to determine the proposed purchasing solution by ensuring, based upon prior purchases of the medication pursuant to the wholesaler/prime vendor program, that the correct quantity of the medication is purchased pursuant to the wholesaler/prime vendor program.

15. A computing system according to claim 8 wherein the information regarding the unified purchasing solution is caused to be provided in real time or near real time relative to receipt of the order.

16. A computing system configured to address a premium paid pursuant to a wholesaler/prime vendor program, the computing system comprising processing circuitry and at least one memory including computer program code, the at least one memory and the computer program code configured to, with the processing circuitry, cause the computing system to at least:
    access data of a supplier of one or more medications to determine a price of the one or more medications pursuant to a plurality of pricing programs;
    determine a price of one or more medications that are purchased pursuant to the wholesaler/prime vendor program;
    determine a price of the one or more medications in the event that the one or more medications had alternatively been purchased pursuant to a group purchasing organization (GPO) program;
    determine the premium for a respective one of the one or more medications that is paid pursuant to the wholesaler/prime vendor program relative to the GPO program; and
    cause a presentation to be provided upon a user interface including information regarding one or more causes for the premium and information regarding one or more potential solutions to reduce the premium, wherein the one or more causes are at least partially based upon the respective medication and a type of health care provider that is purchasing the respective medication.

17. A computing system according to claim 16 wherein the at least one memory and the computer program code are configured to, with the processing circuitry, cause the computing system to cause the presentation to the provided by causing information to be presented regarding the one or more medications and the premiums determined for the respective medications.

18. A computing system according to claim 16 wherein the at least one memory and the computer program code are configured to, with the processing circuitry, cause the computing system to cause information to be presented by causing the information regarding the one or more medications to be presented in a ranked order based upon the premiums determined for the respective medications.

19. A computing system according to claim 16 wherein the information regarding one or more causes for the premium comprise information regarding why the respective medication was purchased pursuant to the wholesaler/prime vendor program instead of the GPO program.

* * * * *